United States Patent
Yoshikawa et al.

(10) Patent No.: US 10,677,751 B2
(45) Date of Patent: Jun. 9, 2020

(54) SENSOR CALIBRATION DEVICE AND SENSOR CALIBRATION METHOD

(71) Applicant: Yokogawa Electric Corporation, Musashino-shi, Tokyo (JP)

(72) Inventors: Masahide Yoshikawa, Tokyo (JP); Tomoaki Eto, Tokyo (JP); Shouji Igarashi, Tokyo (JP); Yuichi Nozaka, Tokyo (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 177 days.

(21) Appl. No.: 15/914,020

(22) Filed: Mar. 7, 2018

(65) Prior Publication Data
US 2018/0259479 A1 Sep. 13, 2018

(30) Foreign Application Priority Data
Mar. 9, 2017 (JP) .................. 2017-044776

(51) Int. Cl.
G01N 27/416 (2006.01)
G01N 33/00 (2006.01)

(52) U.S. Cl.
CPC ..... G01N 27/4165 (2013.01); G01N 27/4163 (2013.01); G01N 27/4167 (2013.01); G01N 33/0006 (2013.01)

(58) Field of Classification Search
CPC .......... G01N 27/4165; G01N 27/4163; G01N 27/4167; G01N 33/0006; G01N 27/00; G01D 18/00
USPC ................................. 324/251, 438
See application file for complete search history.

(56) References Cited

U.S. PATENT DOCUMENTS

| 5,659,125 A | 8/1997 | Ernst |
| 2010/0326165 A1 | 12/2010 | Rauworth et al. |
| 2013/0074575 A1 | 3/2013 | Duric et al. |
| 2015/0070007 A1* | 3/2015 | Kurniawan ............ G01R 35/00 324/251 |

OTHER PUBLICATIONS

Yokogawa Electric Corporation, pH and ORP Sensors, General Specifications, GS 12B07B02-E 13th Edition 2016.05.23-00,Nov. 1999, 1st edition, May 2016, 34 pages, Tokyo, Japan. Internet<https://www.yokogawa.co.jp/pdf/provide/J/GW/GS/0000007298/0/GS12B07B02-00.pdf>.

* cited by examiner

Primary Examiner — Farhana A Hoque
(74) Attorney, Agent, or Firm — Sughrue Mion, PLLC

(57) ABSTRACT

A sensor calibration device for calibrating a sensor device, includes a sensor reader configured to read, from a reference sensor, a physical quantity which is a reference of a calibration and detected by the reference sensor, and a sensor manager configured to convert the physical quantity read by the sensor reader into a reference measurement value, the sensor manager being configured to obtain a calibration target measurement value obtained by the sensor device measuring the physical quantity, and the sensor manager being configured to output, to the sensor device, a calibration instruction based on the reference measurement value and the calibration target measurement value.

18 Claims, 6 Drawing Sheets

SENSOR CALIBRATION DEVICE AND SENSOR CALIBRATION METHOD

BACKGROUND

Technical Fields

The present invention relates to a sensor calibration device and a sensor calibration method.

Priority is claimed on Japanese Patent Application No. 2017-044776, filed Mar. 9, 2017, the contents of which are incorporated herein by reference.

Related Art

In a plant having various facilities, various sensors for detecting a predetermined physical quantity are installed in each facility placed in the plant. In the plant, operation state of a facility and quality of products produced in the facility are managed based on measurement values representing physical quantities output from the sensors installed in each facility.

In order to maintain normal operation (normality) of the facility that is installed in the plant, routine inspection work and work for dealing with troubles such as failures and defects are performed to each facility. In the inspection work in the plant, not only the operation state of the facility is inspected, but also work such as sensor calibration is performed. In the sensor calibration, a sensor installed in the facility and a reference sensor detect the same physical quantity, and a coefficient of a conversion formula (conversion coefficient) used when converting the physical quantity detected by the sensor installed in the facility into a measurement value is corrected. Thus, a measurement value representing the physical quantity detected by the sensor installed in the facility can be adjusted to be the same value as a measurement value representing the physical quantity detected by the reference sensor.

For example, the sensor is a pH sensor of glass tube type that detects a hydrogen ion concentration (pH), and a sensor device includes a pH sensor which is a calibration target installed in the facility and a converting device that performs a conversion process for converting an analog physical quantity (for example, voltage value), which is detected and output by the pH sensor, into a measurement value (pH value). In this case, in the calibration of the sensor device, first, both a measuring device to which the reference pH sensor is connected and the sensor device measure a reference buffer fluid whose value of hydrogen ion concentration (pH value) is known beforehand. Specifically, both the reference pH sensor connected to the measuring device and the pH sensor of the calibration target included in the sensor device are immersed in the reference buffer fluid to detect the pH value of the same buffer fluid. If the pH value of the buffer fluid measured by the measuring device is different from the pH value of the buffer fluid measured by the sensor device, a conversion coefficient (for example, a conversion coefficient of an intercept and a slope) of a conversion formula (Voltage-pH value conversion formula) used for the conversion process by the converting device is corrected (changed) so that the pH value of the buffer fluid measured by the sensor device can be adjusted to be the same value as the pH value of the buffer fluid measured by the measuring device.

In the plant, a field operator, who performs various operations on the placed facility, performs work for calibrating the sensor device as described above. For this reason, the field operator carries the measuring device, goes to the facility where the sensor device including the sensor of the calibration target is connected, and measure the pH value of the buffer fluid while both the reference pH sensor connected to the measuring device carried by the field operator and the pH sensor of the calibration target are immersed in the buffer fluid. Thereafter, the field operator corrects (changes) the conversion coefficient of the converting device based on the pH value of the buffer fluid measured by the measuring device.

Incidentally, since various facilities are installed in a plant, a plurality of sensors are installed. In recent years, a converting device, which can be connected to a plurality of sensors and can perform a conversion process of converting physical quantities detected and output by the plurality of connected sensors into measurement values respectively corresponding to the physical quantities, has also been put to practical use (commercialized). In this case, the sensor device can be configured by connecting (concentrating) the plurality of sensors to one converting device. For this reason, in a conventional sensor device in which the sensor is connected to the converting device in one-to-one, it is conceivable that the sensor and the converting device are disposed close to each other. However, in a case of a recent sensor device in which a plurality of sensors can be connected (concentrated) to one converting device, the sensors may be installed at a position away from the converting device. In this case, for example, it is conceivable that any one of the sensors included in the sensor device is installed at a distance of several meters to several tens of meters from the converting device.

For example, in "General specifications of pH and ORP sensors", Yokogawa Electric Corporation, GS 12B07B02 13th Edition 2016.05.23-00, 1999.11 first edition, 2016.05 13th edition, Internet, <https://www.yokogawa.co.jp/pdf/provide/J/GW/GS/0000007298/0/GS12B07B02-00.pdf>, it is described that there is a pH sensor having a cable length of 20 meters in a sensor device including a pH sensor and a converting device. Therefore, by using the pH sensor described in "General specifications of pH and ORP sensors", a sensor device in which the pH sensor is installed at a distance of 20 meters from the converting device can be constituted. If such a sensor device is installed in the facility, a field operator who performs a calibration work of the sensor device in the plant calibrates the sensor device while the field operator moves a plurality of times between a position where the pH sensor of the calibration target is installed and a position where the converting device is installed.

FIG. 6 is a drawing illustrating an example of a procedure of calibrating the sensor device using a conventional measuring device. FIG. 6 schematically shows the work of calibrating the sensor device performed by the field operator in a case where the sensor and the converting device included in the sensor device installed in the facility in the plant are installed at distant positions respectively. In the plant, the field operator performs the work of calibrating the sensor device in the following procedure.

(Procedure P1): The field operator FO, who performs the calibration work of the sensor device in the plant, carries a measuring device RM connected to a reference pH sensor RS (hereinafter, called as "reference sensor RS"), and goes to a position where a pH sensor CS of the calibration target (hereinafter, called as "calibration target sensor CS") included in the sensor device is installed. Thereafter, the field operator FO immerses both the reference sensor RS and the calibration target sensor CS in a buffer fluid.

(Procedure P2): The field operator FO measures with the measuring device RM while both the reference sensor RS and the calibration target sensor CS are immersed in the buffer fluid. Then, the field operator FO waits until the pH value of the buffer fluid indicated by the measuring device RM becomes stable (in other words, the detection of the pH value of the buffer fluid by the reference sensor RS becomes stable), and then the field operator FO obtains the pH value of the buffer fluid indicated by the measuring device RM. For example, the field operator FO writes the pH value of the buffer fluid stably displayed on the measuring device RM on a paper medium such as a work sheet.

(Procedure P3): The field operator FO brings the paper medium on which the pH value is written and goes to the position where the converting device CV included in the sensor device is installed. At this time, for example, if the calibration target sensor CS and the converting device CV included in the sensor device are installed at a distance of 20 meters from each other, the field operator FO moves by 20 meters.

(Procedure P4): The field operator FO corrects (changes) the conversion coefficient of the converting device CV based on the pH value written on the paper medium which has been brought. For example, when calibrating the converting device CV, the field operator FO corrects (changes) the conversion coefficient of the converting device CV by manually inputting the pH value written on the paper medium which has been brought.

(Procedure P5): The field operator FO checks the pH value displayed on the converting device CV. For example, the field operator FO causes the converting device CV to perform a normal measurement, and checks whether the pH value currently displayed on the converting device CV is the same as the pH value written on the paper medium which has been brought.

(Procedure P6): If the pH value written on the paper medium which has been brought and the pH value displayed on the converting device CV are the same value (in other words, if the correction (change) of the conversion coefficient of the converting device CV has been performed normally), the field operator FO returns to the position where the calibration target sensor CS is installed. At this time, for example, when the calibration target sensor CS and the converting device CV included in the sensor device are installed at a distance of 20 meters from each other, the field operator FO moves again by 20 meters.

(Procedure P7): The field operator FO checks whether or not the pH value displayed on the measuring device RM is the same as the pH value displayed on the converting device CV (in other words, whether or not the pH value of the buffer fluid indicated by the measuring device RM is not changed). If the pH value displayed on the measuring device RM and the pH value displayed on the converting device CV are the same value, the field operator FO determines that the calibration has been performed correctly. Then, the field operator FO returns the calibration target sensor CS immersed in the buffer fluid to an original position (in other words, installs the calibration target sensor CS again in the facility where the calibration target sensor CS was installed), and ends the calibration work of the sensor device.

Thus, in a plant in which the sensor and the converting device included in the sensor device are installed at positions separated from each other, the field operator performs the work of calibrating the sensor device while moving between the sensor and the converting device. The above-described operation procedure for calibrating the sensor device is a procedure of so-called one-point calibration in which calibration is performed based on one type of buffer fluid. In the one-point calibration, it is possible to correct (change) a conversion coefficient of an intercept in the conversion formula used by the converting device for the conversion process.

However, in the calibration of the sensor device in the plant, so-called two-point calibration and three-point calibration, in which two or three types of buffer fluids are used among various types of reference buffer fluids whose pH values are known beforehand, such as pH value=4, pH value=7, pH value=9, and so on, are performed. In the two-point calibration, it is possible to correct (change) a conversion coefficient of a slope in addition to the intercept in the conversion formula used by the converting device for the conversion process. Further, in the three-point calibration, the range of the pH value that can be measured by the sensor device can be made wider by using an approximation formula of two broken lines represented by three points. However, in this case, the field operator who performs the calibration work of the sensor device repeats the above-described procedures P1 to P7 as many as the number of types of the buffer fluids used for calibration. In other words, the field operator performing the calibration work of the sensor device further moves (reciprocates) between the sensor of the calibration target and the converting device included in the sensor device in accordance with the number of types of buffer fluids used for calibration.

As described above, if the sensor and the converting device included in the sensor device in the plant are installed at positions separated from each other, the field operator has to move (reciprocate) between their positions to perform the calibration of the sensor device. That is, the calibration of the sensor device in the plant in which the sensor and the converting device included in the sensor device are installed at positions separated from each other is a work requiring the field operator to move. For this reason, the work of calibrating the sensor device is troublesome for the operator. Especially, if the field operator has to move a long distance to perform the calibration work of the sensor device, it becomes more troublesome. Moreover, in the work of calibrating the sensor device, as described above, since the conversion coefficient of the converting device is corrected (changed) manually, an erroneous operation may be performed. If the operator corrects (changes) the conversion coefficient of the converting device to an erroneous value, the field operator has to further move (reciprocate) between the respective positions of the sensor and the converting device in order to correct the erroneous correction (change) and to confirm a calibration result.

It is also conceivable that two field operators perform the work procedures for calibrating the sensor device as described above. Specifically, it is conceivable that one field operator visits the position where the sensor included in the sensor device is installed, and another field operator visits the position where the converting device is installed, in order to perform the work procedures for calibrating the sensor device while two field operators contact each other. However, in this case, although it is possible to solve the troublesome problem about the movement of the field operator, for example, it is possible to correct (change) the conversion coefficient of the converting device to an incorrect value due to a communication mistake of the pH value or the like. In this case, it is considered that the man-hour of the work in the plant is increased.

SUMMARY

A sensor calibration device for calibrating a sensor device, may include a sensor reader configured to read, from a reference sensor, a physical quantity which is a reference of a calibration and detected by the reference sensor, and a sensor manager configured to convert the physical quantity read by the sensor reader into a reference measurement value, the sensor manager being configured to obtain a calibration target measurement value obtained by the sensor device measuring the physical quantity, and the sensor manager being configured to output, to the sensor device, a calibration instruction based on the reference measurement value and the calibration target measurement value.

Further features and aspects of the present disclosure will become apparent from the following detailed description of exemplary embodiments with reference to the attached drawings.

DETAILED DESCRIPTION OF THE EMBODIMENTS

The embodiments of the present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

An aspect of the present invention is to provide a sensor calibration device and a sensor calibration method capable of calibrating a sensor device installed in a facility disposed in a plant more efficiently and accurately.

Figure 1:
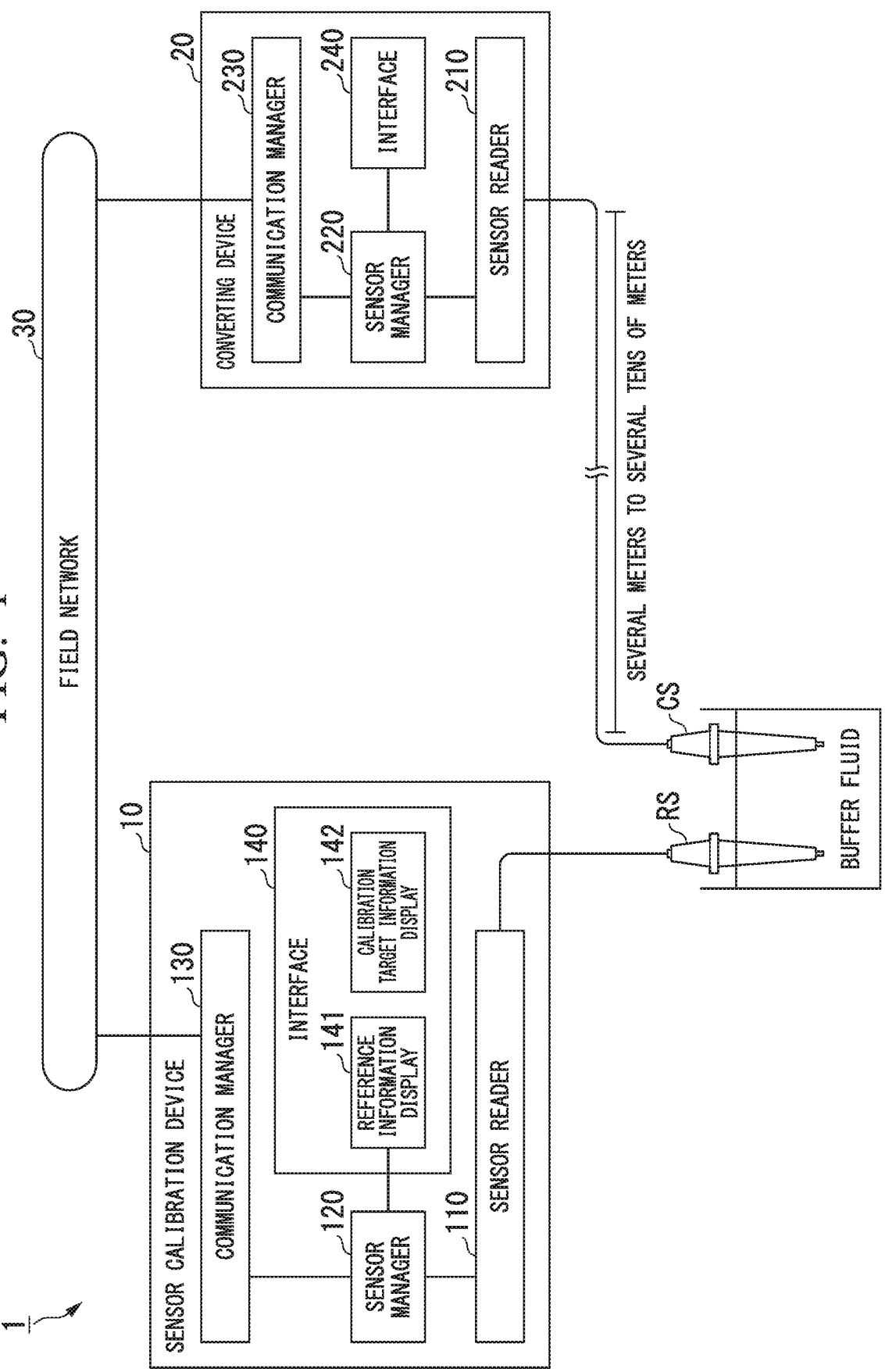
FIG. 1 is a block diagram illustrating a schematic configuration of a sensor calibration device and a schematic configuration of a sensor calibration system constructed for the calibration performed by the sensor calibration device according to an embodiment of the present invention.

Hereinafter, embodiments of the present invention will be described with reference to the drawings. FIG. 1 is a block diagram illustrating a schematic configuration of a sensor calibration device and a schematic configuration of a sensor calibration system constructed for the calibration performed by the sensor calibration device according to an embodiment of the present invention. FIG. 1 shows a sensor calibration device (reference measuring device) 10 to which a sensor RS (hereinafter, called as "reference sensor RS") used as a calibration standard is connected. The reference sensor RS is a sensor for detecting characteristics of a liquid product or a semi-product. Moreover, FIG. 1 shows a sensor device, in which a sensor CS of a calibration target (hereinafter, called as "calibration target sensor CS") and a converting device 20 are connected to each other, as a sensor device of a target (calibration target) calibrated by the sensor calibration device 10. For example, the calibration target sensor CS is a sensor similar to the reference sensor RS for detecting characteristics of a liquid product or a semi-product, such as industrial water and chemicals produced in a facility. FIG. 1 shows a state in which the sensor calibration device 10 calibrates the sensor device of the calibration target using a field network 30 as a communication means. Specifically, FIG. 1 shows a state in which the sensor calibration device 10 and the converting device 20 included in the sensor device of the calibration target are connected via the field network 30 in order to construct a sensor calibration system 1 for calibrating the sensor device by the sensor calibration device 10.

The field network 30 is a wired or wireless dedicated communication network constructed in the plant in order to connect facilities disposed in the plant with a higher-level control system for controlling operation state of the facilities in the plant. The higher-level control system is, for example, a distributed control system (DCS) or the like. Communication standards applied to the field network 30 may be various kinds of communication standards or methods applied in the plant, for example, an industrial wireless standard such as ISA100.11a, a wireless standard such as a sensor network system, a communication standard in which wireless communication and wired communication are mixed, such as Wireless/Wired HART (registered trademark), a communication standard of master/slave type, such as MODBUS (registered trademark), a field bus standard such as FOUNDATION (registered trademark) fieldbus, PROFIBUS (PROCESS FIELD BUS) (registered trademark), or the like.

In addition to an industrial plant that refines petroleum and produces chemical products, the plant includes a plant that manages and controls a well (for example, a gas field and an oil field) and its surroundings, a plant that manages and controls power generation (for example, hydropower, thermal power, and nuclear power), a plant that manages and controls environmental power generation (for example, solar power and wind power), a plant that manages and controls a water supply and sewerage system, a dam, and so on.

First, the configuration of the sensor calibration device 10 will be described. The sensor calibration device 10 is connected to the sensor device of the calibration target via the field network 30, and the sensor calibration device 10 calibrates the connected sensor device based on a measurement value representing the physical quantity detected and output by the reference sensor RS. In other words, the sensor calibration device 10 is remotely connected to the sensor device of the calibration target via the field network 30, and the sensor calibration device 10 calibrates the sensor device by remote control based on the measurement value representing the physical quantity detected and output by the reference sensor RS. As described above, the reference sensor RS is a sensor used as a reference when the sensor calibration device 10 calibrates the sensor device, and the reference sensor RS detects a predetermined analog physical quantity and outputs a signal representing the detected physical quantity (analog quantity) to the sensor calibration device 10.

As an example, FIG. 1 shows a case where each of the reference sensor RS and the calibration target sensor CS is a hydrogen ion concentration (pH) sensor of glass tube type.

In this case, each of the reference sensor RS and the calibration target sensor CS outputs a voltage value representing the detected hydrogen ion concentration (pH). The sensor calibration device 10 calibrates the calibration target sensor CS by adjusting the pH value output as the measurement value by the sensor device, in which the calibration target sensor CS detects the reference buffer fluid whose hydrogen ion concentration value (pH value) is known beforehand, to be the same value as the pH value detected by the reference sensor RS which detects the same reference buffer fluid.

In FIG. 1, the reference sensor RS is a pH sensor of glass tube type, but the reference sensor RS is not limited to the pH sensor as shown in FIG. 1. The reference sensor RS may be any sensor as long as it is a sensor that detects a physical quantity of the same liquid substance detected by the calibration target sensor CS. That is, the reference sensor RS and the calibration target sensor CS may be any sensors as long as they are sensors that detect the same physical quantity. For example, in addition to the pH sensor shown in FIG. 1, the reference sensor RS and the calibration target sensor CS may be various types of sensors for measuring a liquid substance, such as an oxidation reduction potential (ORP) sensor, a conductivity sensor, a dissolved oxygen (DO) sensor, a residual chlorine sensor, a turbidity sensor, a temperature sensor, or the like. The reference sensor RS and the calibration target sensor CS are not limited to the above-described sensors for measuring a liquid substance.

The sensor calibration device 10 includes a sensor reader 110, a sensor manager 120, a communication manager 130, and an interface (I/F) 140.

The sensor reader 110 reads a voltage value representing a pH value of the reference buffer fluid output from the connected reference sensor RS. The sensor reader 110 outputs the voltage value read from the reference sensor RS to the sensor manager 120.

The sensor manager 120 is a controller that controls a whole of the sensor calibration device 10. The sensor manager 120 converts the voltage value output from the sensor reader 110 based on a predetermined conversion formula (voltage-pH value conversion formula) to calculate the pH value of the reference buffer fluid. The sensor manager 120 outputs, to the interface 140, the calculated pH value as a reference measurement value (hereinafter, called as "reference pH value") to cause the interface 140 to display the reference pH value. In the present invention, the conversion formula, used by the sensor manager 120, for converting the voltage value output from the sensor reader 110 to the reference pH value is not particularly specified.

In the calibration process in which the sensor calibration device 10 calibrates the sensor device, the sensor manager 120 obtains, as a calibration target measurement value (Hereinafter, called as "calibration target pH value"), a pH value of the reference buffer fluid calculated by the converting device 20 based on the voltage value output from the calibration target sensor CS, via the communication manager 130 and the field network 30. Thereafter, the sensor manager 120 outputs the obtained calibration target pH value to the interface 140 to cause the interface 140 to display the calibration target pH value. Then, the sensor manager 120 calibrates the sensor device in response to an instruction from the field operator who performs a calibration work of the sensor device in the plant.

Specifically, in the calibration process for calibrating the sensor device, the sensor manager 120 outputs (transmits) an instruction for outputting (transmitting) the calibration target pH value (hereinafter, called as "measurement value output instruction") to the converting device 20 via the communication manager 130 and the field network 30. Then, the sensor manager 120 obtains the calibration target pH value which has been output (transmitted) from the converting device 20 via the field network 30 and the communication manager 130 in response to the output (transmitted) measurement value output instruction. Then, the sensor manager 120 outputs the obtained calibration target pH value to the interface 140 to cause the interface 140 to display the calibration target pH value. Thereafter, in response to an instruction of the field operator, the sensor manager 120 outputs (transmits), to the device 20 via the field network 30 and the communication manager 130, a calibration instruction (hereinafter, called as "conversion coefficient correction instruction") for instructing to correct (change) a conversion coefficient (for example, a conversion coefficient of an intercept and a slope) of the conversion formula (voltage-pH value conversion formula) used in the conversion process in which the converting device 20 converts the voltage value output from the calibration target sensor CS into the pH value. Here, for example, if a difference between the reference pH value and the calibration target pH value is used as the correction amount, the conversion coefficient correction instruction is a calibration instruction for instructing to correct (change) the conversion coefficient of the voltage-pH value conversion formula by the correction amount. Therefore, the sensor manager 120 outputs (transmits), to the converting device 20, information indicating the correction amount as the conversion coefficient correction amount, together with the conversion coefficient correction instruction.

The converting device 20 corrects (changes) the conversion coefficient of the voltage-pH value conversion formula by the correction amount indicated by the conversion coefficient correction amount based on the conversion coefficient correction instruction and the conversion coefficient correction amount output (transmitted) from the sensor manager 120. As a result, the converting device 20 calculates the calibration target pH value by converting, once again, the voltage value detected and output by the calibration target sensor CS. The calibration target pH value is calibrated to be the same value as the reference pH value displayed on the interface 140 in the sensor calibration device 10. The correction amount of the conversion coefficient of the voltage-pH value conversion formula is not limited to the difference between the reference pH value and the calibration target pH value. For example, if the converting device 20 converts, once again, the voltage value detected and output by the calibration target sensor CS, the correction amount of the conversion coefficient of the voltage-pH value conversion formula may be a correction amount calculated by any process or calculation as long as it is a correction amount of a conversion coefficient for converting the voltage value into the calibration target pH value having the same value as the reference pH value (in other words, a conversion coefficient for adjusting the calibration target pH value to be the same value as the reference pH value).

When the sensor manager 120 obtains the calibration target pH value from the converting device 20, the sensor manager 120 may obtain information for identifying the calibration target sensor CS (for example, identification information (ID) of the calibration target sensor CS). In this case, the sensor manager 120 may store and manage the calibration target pH value and the identification information of the calibration target sensor CS obtained from the converting device 20, and information on date and time when calibration of the sensor device was performed, such as date and time when the conversion coefficient correction instruction is output (transmitted) to the converting device 20, and the conversion coefficient correction amount in association with each other. In other words, the sensor manager 120 may store and manage a history of calibration of the sensor device.

The communication manager 130 transmits/receives various kinds of information to/from the converting device 20 via the field network 30. Specifically, when the sensor calibration device 10 performs the calibration process to the sensor device, the communication manager 130 outputs (transmits), to the converting device 20, the measurement value output instruction output from the sensor manager 120. Then, the communication manager 130 obtains (receives) the calibration target pH value output (transmitted) from the converting device 20 via the field network 30 in response to the measurement value output instruction which has been output (transmitted), and the communication manager 130 outputs the obtained (received) calibration target pH value to the sensor manager 120. Further, the communication manager 130 outputs (transmits) the conversion coefficient correction instruction and the conversion coefficient correction amount, which have been output from the sensor manager 120, to the converting device 20 via the field network 30.

The interface 140 generates a display screen for showing the field operator information about the reference pH value calculated by the sensor manager 120 and the calibration target pH value obtained from the converting device 20, and the interface 140 displays the generated display screen. The interface 140 includes a reference information display 141, a calibration target information display 142, and a display device such as a liquid crystal display (LCD: Liquid Crystal Display).

The reference information display 141 generates a display screen (hereinafter, called as "reference sensor information screen") for showing the field operator the information on the reference pH value. The reference information display 141 causes the display device to display the generated reference sensor information screen. The calibration target information display 142 generates a display screen (hereinafter, called as "calibration target sensor information screen") for showing the field operator the information on the calibration target pH value. The calibration target information display 142 causes the display device to display the generated calibration target sensor information screen.

Further, for example, the interface 140 includes buttons, switches, and so on that receive operations performed to the sensor calibration device 10 by the field operator. The operations performed to the sensor calibration device 10 by the field operator include at least an operation for instructing to execute the calibration of the sensor device (hereinafter, called as "calibration execution instruction"). When the interface 140 has received the calibration execution instruction in accordance with the operation performed by the field operator, the interface 140 outputs, to the sensor manager 120, information representing that the calibration execution instruction has been received.

For example, the interface 140 may include a touch panel in which a display device, such as a liquid crystal display, and a detection device for detecting various touch operations (for example, tap or flick) performed by the field operator using a pressure sensor, are combined. In this case, the interface 140 may generate a display screen for displaying a button (hereinafter, called as "calibration execution button") used for inputting the calibration execution instruction by the field operator. The interface 140 displays the generated display screen of the calibration execution button on the display device together with the reference sensor information screen generated by the reference information display 141 and the calibration target sensor information screen generated by the calibration target information display 142. In this case, when the detection device detects that the calibration execution button has been pressed by a tapping operation performed by the field operator, the interface 140 may transmit, to the sensor manager 120, information representing that the calibration execution instruction by the field operator has been received.

In this way, the sensor calibration device 10 communicates with the sensor device of the calibration target installed in a facility via the field network 30, and the sensor calibration device 10 shows the field operator the pH value of the reference calibration buffer fluid, which is measured by the sensor calibration device 10 and whose pH value is known beforehand, and the pH value of the same buffer fluid measured by the sensor device of the calibration target. Further, the sensor calibration device 10 communicates with the sensor device of the calibration target in response to an instruction from the field operator, and the sensor calibration device 10 corrects (changes) the conversion coefficient of the voltage-pH value conversion formula used in the conversion process by the sensor device so that the pH value output as a measurement value from the sensor device of the calibration target becomes the same value as the pH value measured by the sensor calibration device 10. Thereby, the sensor calibration device 10 can calibrate the sensor device.

The sensor calibration device 10 is not limited to a device which realizes only the function of calibrating the sensor device of the calibration target connected via the field network 30 based on the measurement value indicating the physical quantity detected and output by the reference sensor RS. For example, the sensor calibration device 10 is may be a portable terminal device (maintenance terminal device) used by a field operator who performs daily inspection work, maintenance work, and work for dealing with troubles of facilities such as failures and defects, for facilities disposed in the plant. As a function of the portable terminal device (maintenance terminal device), a function of calibrating a sensor device of the calibration target may be implemented.

Next, the configuration of the sensor device which is a target of the calibration performed by the sensor calibration device 10 will be described. As described above, in the sensor device, the calibration target sensor CS and the converting device 20 are connected to each other. That is, the sensor device is constituted by a combination of the calibration target sensor CS and the converting device 20. In the sensor device, at least the calibration target sensor CS is installed at a position where a predetermined physical quantity (pH value in FIG. 1) is detected in the facility disposed in the plant, and the converting device 20 is connected to the field network 30. In the plant, the converting device 20 included in the sensor device is not necessarily installed at a position close to the calibration target sensor CS. In the example shown in FIG. 1, the calibration target sensor CS and the converting device 20 are installed at a position separated from each other by several meters to several tens of meters (for example, a position separated from each other by 20 meters).

In a normal operation, the calibration target sensor CS outputs, to the converting device 20, the detected voltage value representing a hydrogen ion concentration (pH) of a liquid product or a semi-product, and the converting device 20 converts the voltage value into a measurement value (pH value). The sensor device outputs (transmits) the measurement value (pH value) converted by the converting device 20 to a higher-level control system, such as a distributed control system, via the field network 30.

On the other hand, when the sensor calibration device 10 performs the calibration (calibration process), the converting device 20 included in the sensor device is connected to the sensor calibration device 10 via the field network 30. In the sensor device, the calibration target sensor CS detects the same buffer fluid as the reference buffer fluid measured by the sensor calibration device 10, and the calibration target sensor CS outputs a voltage value representing the hydrogen ion concentration (pH). The converting device 20 converts the voltage value output from the calibration target sensor CS into a pH value. The converting device 20 outputs (transmits) the converted pH value, as the calibration target pH value, to the sensor calibration device 10 via the field network 30 in response to the measurement value output instruction which has been output (transmitted) from the sensor calibration device 10. Thereafter, based on the conversion coefficient correction instruction and the conversion coefficient correction amount which have been output (transmitted) from the sensor calibration device 10, the converting device 20 corrects (changes) the conversion coefficient of the voltage-pH value conversion formula used in the conversion process for converting, into the pH value, the voltage value representing the hydrogen ion concentration (pH) output from the calibration target sensor CS. Thus, if the calibration target sensor CS measures the same buffer fluid as that of the sensor calibration device 10, the sensor device is calibrated to output the same pH value (calibration target pH value) as the pH value (reference pH value) output by the sensor calibration device 10. Then, in the sensor device, the converting device 20 converts the voltage value representing the same hydrogen ion concentration (pH) by using the voltage-pH value conversion formula obtained by correcting (changing) the conversion coefficient, and the converting device 20 outputs (transmits) the converted pH value, as a calibration target pH value after calibration, to the sensor calibration device 10 via the field network 30.

In the sensor device, the converting device 20 includes a sensor reader 210, a sensor manager 220, a communication manager 230, and an interface (I/F) 240.

In a normal operation, the sensor reader 210 reads a voltage value representing a pH value of a liquid product or a semi-product output from the connected calibration target sensor CS. Moreover, when the sensor calibration device 10 performs the calibration (calibration process), the sensor reader 210 reads a voltage value representing the pH value of the same reference buffer fluid as that of the sensor calibration device 10. The sensor reader 210 outputs the voltage value read from the calibration target sensor CS to the sensor manager 220.

The sensor manager 220 is a controller that controls a whole of the sensor calibration device 10. The sensor manager 220 converts the voltage value output from the sensor reader 210 based on the predetermined voltage-pH value conversion formula to calculate the pH value. In the normal operation, the sensor manager 220 converts the voltage value representing the pH value of the liquid product or the semi-product, which has been output from the sensor reader 210, to calculate the pH value. Then, the sensor manager 220 outputs (transmits) the calculated pH value to a higher-level control system via the communication manager 230 and the field network 30. Moreover, the sensor manager 220 outputs the calculated pH value to the interface 240 to cause the interface 240 to display the calculated pH value.

On the other hand, when the sensor calibration device 10 performs the calibration (calibration process), the sensor manager 220 converts the voltage value representing the pH value of the reference buffer fluid output from the sensor reader 210 to calculate the PH value (calibration target PH value), and the sensor manager 220 outputs the calculated calibration target pH value to the interface 240 to cause the interface 240 to display the calibration target pH value. Moreover, when the sensor calibration device 10 performs the calibration (calibration process), the sensor manager 220 outputs (transmits) the calculated calibration target pH value to the sensor calibration device 10 via the communication manager 230 and the field network 30 in response to the measurement value output instruction which has been output (transmitted) from the sensor calibration device 10. Furthermore, when the sensor calibration device 10 performs the calibration (calibration process), the sensor manager 220 corrects (changes) the conversion coefficient of the voltage-pH value conversion formula for converting the voltage value representing the pH value output from the sensor reader 210 based on the conversion coefficient correction instruction and the conversion coefficient correction amount which have been output (transmitted) from the sensor calibration device 10. Thereby, the voltage-pH value conversion formula used in the conversion process by the sensor manager 220 is calibrated to become a conversion formula for converting the voltage value into the same value as the reference pH value measured by the sensor calibration device 10 when the voltage value representing the pH value of the reference buffer fluid output from the sensor reader 210 has been converted once again. As a result, also in a succeeding normal operation, the sensor manager 220 performs the conversion process of converting the voltage value representing the pH value output from the sensor reader 210 into the pH value by using the calibrated voltage-pH value conversion formula. In the present invention, the conversion formula used by the sensor manager 220 for converting the voltage value output from the sensor reader 210 into the pH value (including the reference pH value) is not particularly specified. For confirmation, the sensor manager 220 converts, once again, the voltage value representing the pH value of the reference buffer fluid using the calibrated voltage-pH value conversion formula to calculate the calibration target pH value. Thereafter, the sensor manager 220 outputs (transmits) the calculated calibration target pH value to the sensor calibration device 10 via the communication manager 230 and the field network 30.

The communication manager 230 transmits/receives various kinds of information to/from the sensor calibration device 10 (specifically, the communication manager 130 provided in the sensor calibration device 10) via the field network 30. Specifically, in a normal operation, the communication manager 230 outputs (transmits) the pH value, which has been output from the sensor manager 220, to a higher-level control system via the field network 30. Moreover, in a normal operation, the communication manager 230 outputs, to the sensor manager 220, control information of the sensor device, such as a measurement condition output (transmitted) from the higher-level control system via the field network 30. In the sensor device, the sensor manager 220 may correct (change) the conversion coefficient (for example, a conversion coefficient of an intercept and a slope) of the voltage-pH value conversion formula used for the conversion process based on an instruction from the higher-level control system.

Moreover, when the sensor calibration device 10 performs the calibration (calibration process), the communication manager 230 obtains (receives) the measurement value output instruction output (transmitted) from the sensor calibration device 10 via the field network 30, and outputs the obtained (received) measurement value output instruction to the sensor manager 220. Then, the communication manager 230 outputs (transmits), to the sensor calibration device 10 via the field network 30, the calibration target pH value which has been output from the sensor manager 220 in response to the measurement value output instruction. Furthermore, the communication manager 230 obtains (receives) the conversion coefficient correction instruction and the conversion coefficient correction amount which have been output (transmitted) from the sensor calibration device 10 via the field network 30, and the communication manager 230 outputs, to the sensor manager 220, the obtained (received) conversion coefficient correction instruction and the conversion coefficient correction amount. Then, when the calibration target pH value after calibration, which has been obtained by converting, once again, the voltage value output from the calibration target sensor CS by using the voltage-pH value conversion formula calibrated based on the conversion coefficient correction instruction and the conversion coefficient correction amount, has been output from the sensor manager 220, the communication manager 230 outputs (transmits) the calibration target pH value after calibration, which has been output from the sensor manager 220, to the sensor calibration device 10 via the field network 30.

The interface 240 generates a display screen for showing the field operator a pH value in the normal operation calculated by the sensor manager 220 and information on the calibration target pH value in the operation when the calibration (calibration process) has been performed by the sensor calibration device 10. For example, the interface 240 includes a display device such as a liquid crystal display (LCD: Liquid Crystal Display). Moreover, for example, the interface 240 includes buttons, switches, and so on that receive operations performed to the converting device 20 by the field operator. When the interface 240 receives an operation performed by the field operator, the interface 240 outputs information on the received operation to the sensor manager 220. The sensor manager 220 of the sensor device may also correct (change) the conversion coefficient of the voltage-pH value conversion formula used for the conversion process in accordance with an operation performed to the interface 240 by the field operator.

For example, the interface 240 may include a touch panel in which a display device, such as a liquid crystal display, and a detection device for detecting various touch operations (for example, tap or flick) performed by the field operator using a pressure sensor, are combined.

As described above, in the plant, the converting device 20 included in the sensor device is not necessarily installed at a position close to the calibration target sensor CS (in other words, close to a position where the field operator immerses, into the reference buffer, both the reference sensor RS and the calibration target sensor CS in the work of calibrating the sensor device). In the sensor calibration device 10, the calibration target pH value, which has been output (transmitted) from the converting device 20 via the field network 30, is displayed on the display device of the interface 140. For this reason, if the calibration target sensor CS and the converting device 20 are installed away from each other, it is not necessary for the field operator to move to check the calibration target pH value displayed on the display device of the interface 240 provided in the converting device 20 in the work of calibrating the sensor device. Therefore, the interface 240 does not need to display, on the display device, the display screen showing the information on the calibration target pH value in the operation when the sensor calibration device 10 performs the calibration (calibration process). However, it is conceivable that the field operator checks the pH value displayed on the display device of the interface 240 in a normal operation, such as daily inspection work in the plant. Therefore, the interface 240 may switch between display and non-display of the display screen on the display device based on a current operation state.

In this way, the sensor device (specifically, the converting device 20) corrects (changes) the conversion coefficient of the voltage-pH value conversion formula used in the conversion process for converting, into the pH value, the voltage value representing the hydrogen ion concentration (pH) output from the calibration target sensor CS in accordance with the measurement value output instruction, the conversion coefficient correction instruction, and the conversion coefficient correction amount, which have been output (transmitted) from the sensor calibration device 10 via the field network 30. Thereby, the sensor device is calibrated so that the pH value output as the measurement value becomes the same value as the pH value measured by the sensor calibration device 10.

As described above, in the sensor calibration system 1, the measurement value measured by the sensor device connected via the field network 30 can be displayed on the sensor calibration device 10 in the calibration process of calibrating the sensor device of the calibration target by the sensor calibration device 10. In the sensor calibration system 1, the calibration of the sensor device can be performed by operating the sensor calibration device 10. For this reason, the field operator who performs the work of calibrating the sensor device in the plant immerses both the reference sensor RS and the calibration target sensor CS into the reference buffer fluid at a position where the calibration target sensor CS included in the sensor device is installed, and operates the sensor calibration device 10 in this state in order to perform the calibration work for the sensor device of the calibration target via the field network 30. Therefore, in the sensor calibration system 1, even if the converting device 20 included in the sensor device of the calibration target is installed away from the position where the calibration target sensor CS is installed, the calibration of the sensor device can be performed without the field operator moving (reciprocating) between a position where the calibration target sensor CS is installed and a position where the converting device 20 is installed.

Furthermore, in the sensor calibration system 1, the sensor calibration device 10 outputs (transmits) the conversion coefficient correction amount together with the conversion coefficient correction instruction to the converting device 20 included in the sensor device of the calibration target via the field network 30. Thereafter, the converting device 20 corrects (changes) the conversion coefficient of the conversion formula based on the conversion coefficient correction instruction and the conversion coefficient correction amount which have been output (transmitted) via the field network 30. Therefore, in the sensor calibration system 1, it is not necessary for the field operator to manually input a conversion coefficient into the converting device 20 to correct (change) it, and a factor of erroneous correction (change) can be eliminated.

In this way, since the sensor calibration device 10 that can be connected to the sensor device via the field network 30 is used when calibrating the sensor device of the calibration target, the calibration of the sensor device installed in the facility disposed in the plant can be performed more efficiently. In other words, in the sensor calibration system 1, the sensor device is calibrated using the sensor calibration device 10 so that troublesome work for the field operator can be eliminated.

Figure 2:
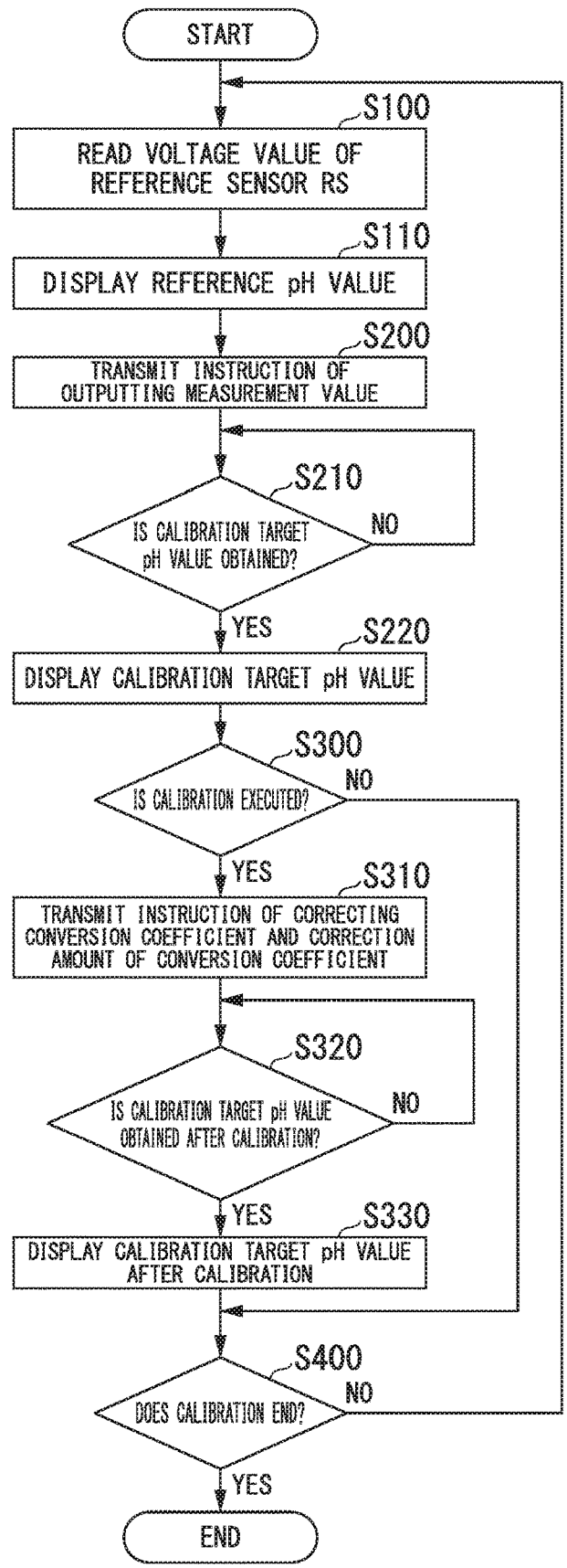
FIG. 2 is a flowchart which shows an example of a procedure for calibrating the sensor device in the sensor calibration device according to the embodiment of the present invention.

Next, a procedure of the calibration process for calibrating the sensor device of the calibration target using the sensor calibration device 10 will be described. FIG. 2 is a flowchart which shows an example of a procedure (calibration process) for calibrating the sensor device (in other words, the sensor device including the calibration target sensor CS and the converting device 20) in the sensor calibration device 10 according to the embodiment of the present invention. The calibration process of the sensor device, which is shown in FIG. 2 and performed by the sensor calibration device 10, is started in accordance with an instruction of the field operator, after the field operator goes to the position where the calibration target sensor CS is installed, and both the reference sensor RS and the calibration target sensor CS are immersed into the reference buffer fluid.

When the sensor calibration device 10 starts the calibration process, first, the sensor reader 110 provided in the sensor calibration device 10 reads a voltage value representing the pH value of the reference buffer fluid from the connected reference sensor RS, and outputs the voltage value to the sensor manager 120 (step S100). The sensor manager 120 converts the voltage value output from the sensor reader 110 based on the predetermined conversion formula (voltage-pH value conversion formula) to calculate a reference pH value, and the sensor manager 120 outputs the calculated reference pH value to the interface 140 (specifically, the reference information display 141) provided in the sensor calibration device 10.

Next, the reference information display 141 generates a reference sensor information screen for showing the reference pH value output from the sensor manager 120, and the reference information display 141 causes the display device to display the generated reference sensor information screen (step S110). As a result, the reference pH value information is shown to the field operator.

The sensor manager 120 outputs, to the communication manager 130, a measurement value output instruction for instructing the sensor device of the calibration target to output (transmit) the calibration target pH value measured by the calibration target sensor CS (step S200). As a result, the measurement value output instruction is output (transmitted) to the sensor manager 220 via the field network 30 and the communication manager 230 provided in the converting device 20.

Next, the sensor manager 120 determines whether or not the sensor manager 120 has obtained the calibration target pH value output (transmitted) from the sensor manager 220 in accordance with the output (transmitted) measurement value output instruction (step S210). As a result of the determination of step S210, if the sensor manager 120 has not obtained the calibration target pH value (in other words, if the calibration target pH value has not output (transmitted) from the sensor manager 220) (step S210: "NO"), the sensor manager 120 returns to step S210 and waits for obtaining the calibration target pH value output (transmitted) from the sensor manager 220.

On the other hand, as a result of the determination in step S210, if the sensor manager 120 has obtained the calibration target pH value (in other words, if the calibration target pH value has output (transmitted) from the sensor manager 220) (step S210: "YES"), the sensor manager 120 outputs the obtained calibration target pH value to the interface 140 (specifically, the calibration target information display 142).

Next, the calibration target information display 142 generates a calibration target sensor information screen for showing the calibration target pH value output from the sensor manager 120, and causes the display device to display the generated calibration target sensor information screen (step S220). As a result, information on the calibration target pH value is shown to the field operator.

The interface 140 may generate a display screen of the calibration execution button, and may display the generated display screen of the calibration execution button on the display device together with the reference sensor information screen and the calibration target sensor information screen to urge the field operator to input the calibration execution instruction. Moreover, the interface 140 may generate a display screen of a button (hereinafter, called as "calibration cancel button") for inputting not to perform the calibration of the sensor device, and the interface 140 may display it on the display device. Thereby, for example, if it is not necessary for the field operator to perform the calibration of the sensor device using the reference buffer fluid in which both the reference sensor RS and the calibration target sensor CS are currently immersed, the field operator can perform an operation for instructing the sensor calibration device 10 not to perform the calibration process of the sensor device. Furthermore, the interface 140 may generate a display screen of a button (hereinafter, called as "calibration end button") for inputting to end the calibration of the sensor device, and the interface 140 may display it on the display device. Thereby, for example, if the calibration of the sensor device using the reference buffer fluid has been completed, the field operator can perform an operation for instructing the sensor calibration device 10 to end the calibration process of the sensor device.

Next, the sensor manager 120 determines whether or not the calibration execution instruction performed by the field operator has been received (in other words, whether or not the calibration of the sensor device is to be executed) (step S300). For example, the determination in step S300 in the sensor manager 120 can be performed based on information on a selected button, which is output from the interface 140 when the field operator selects one of the calibration execution button and the calibration cancel button displayed on the display device by the interface 140.

The field operator waits until the measurement of the reference buffer fluid performed by using the reference sensor RS and the measurement of the same reference buffer fluid performed by using the calibration target sensor CS become stable (in other words, until the reference pH value and the calibration target pH value become stable), and the field operator performs an operation of a calibration execution instruction. For this reason, in the calibration process of the sensor device, the sensor calibration device 10 sequentially repeats to show, to the field operator, the information on the reference pH value in steps S100 and S110 and the information on the calibration target pH value in steps S200 to S220 in parallel with each other at the same time. Thus, the field operator monitors the reference pH value and the calibration target pH value shown by the sensor calibration device 10 in order to confirm that the measurement of the reference buffer fluid performed by using the reference sensor RS and the measurement of the same reference buffer fluid performed by using the calibration target sensor CS has become stable.

As a result of the determination in step S300, if the calibration of the sensor device is not to be executed (step S300: "NO"), the calibration process of the sensor manager 120 proceeds to step S400. On the other hand, as a result of the determination in step S300, if the calibration of the sensor device is to be executed (step S300: "YES"), the sensor manager 120 outputs (transmits), to the communication manager 130, the conversion coefficient correction instruction of instructing to correct (change) the conversion coefficient of the conversion formula (voltage-pH value conversion formula) used in the conversion process in the converting device 20 and the conversion coefficient correction amount (step S310). As a result, the conversion coefficient correction instruction and the conversion coefficient correction amount are output (transmitted) to the sensor manager 220 via the field network 30 and the communication manager 230.

Consequently, based on the conversion coefficient correction instruction and the conversion coefficient correction amount output (transmitted) from the sensor manager 120, the converting device 20 included in the sensor device corrects (changes) the conversion coefficient of the voltage-pH value conversion formula for converting the voltage value output from the calibration target sensor CS into the pH value. Thereafter, the converting device 20 converts, once again, the voltage value currently output from the calibration target sensor CS using the calibrated voltage-pH value conversion formula, and the converting device 20 outputs (transmits), to the sensor manager 120, the converted calibration target pH value after calibration.

Next, the sensor manager 120 determines whether or not the sensor manager 120 has obtained the calibration target pH value after calibration, which has been output (transmitted) from the sensor manager 220 (step S320). As a result of the determination in step S320, if the sensor manager 120 has not obtained the calibration target pH value after calibration (in other words, if the calibration target pH value after calibration has not been output (transmitted) from the sensor manager 220) (step S320: "NO"), the sensor manager 120 determines that the sensor device has not completed the calibration process (a process of correcting (changing) the conversion coefficient). Then, the sensor manager 120 returns to step S320, and waits for obtaining the calibration target pH value after calibration, which has been output (transmitted) from the manager 220.

On the other hand, as a result of the determination in step S320, if the sensor manager 120 has obtained the calibration target pH value after calibration (in other words, if the calibration target pH value after calibration has been output (transmitted)) from the sensor manager 220) (step S320: "YES"), the sensor manager 120 determines that the sensor device has completed the calibration process (a process of correcting (changing) the conversion coefficient). Then, the sensor manager 120 outputs the obtained calibration target pH value after the calibration to the interface 140 (calibration target information display 142).

Next, the calibration target information display 142 generates a calibration target sensor information screen for showing the calibration target pH value after calibration which has been output from the sensor manager 120, and the calibration target information display 142 displays the generated calibration target sensor information screen on the display device (in other words, updates the calibration target sensor information screen currently displayed on the display device) (step S330). As a result, information on the calibration target pH value after calibration is shown to the field operator, and the field operator can determine whether or not the calibration of the sensor device (the process of correcting (changing) the conversion coefficient) has been performed normally using the reference buffer fluid in which both the reference sensor RS and the calibration target sensor CS are currently immersed.

Next, the sensor manager 120 determines whether or not an instruction for ending the calibration of the sensor device has been received from the field operator (in other words, whether or not to end the calibration of the sensor device) (step S400). In step S400, for example, the sensor manager 120 can determine that the instruction for ending the calibration of the sensor device has been received from the field operator, based on information representing that the calibration end button, which is output from the interface 140 when the calibration end button displayed on the display device by the interface 140 is selected by the operator. As a result of the determination in step S400, if the calibration of the sensor device is ended (step S400: "YES"), the sensor manager 120 ends the calibration process.

On the other hand, as a result of the determination in step S400, if the calibration of the sensor device is not ended (step S400: "NO"), the calibration process of the sensor manager 120 returns to step S100. Then, the sensor calibration device 10 performs the processes from step S100 to step S400 again. Thus, for example, the field operator replaces the reference buffer fluid, in which both the reference sensor RS and the calibration target sensor CS are currently immersed, with a reference buffer fluid of a different pH value, so that the sensor calibration device 10 can perform the calibration of the sensor device again. For example, the field operator uses the sensor calibration device 10 to perform, to the sensor device of the calibration target, so-called two-point calibration or three-point calibration using two or three kinds of buffer fluids among various kinds of reference buffer fluids whose pH values are known beforehand, such as pH value=4, pH value=7, pH value=9, or the like, in order to calibrate the sensor device more accurately.

Through such a process (calibration process), the sensor calibration device 10 corrects (changes) the conversion coefficient of the voltage-pH value conversion formula used in the conversion process by the sensor device of the calibration target connected via the field network 30 to calibrate the sensor device. As a result, even when the converting device 20 included in the sensor device of the calibration target is installed away from the position where the calibration target sensor CS is installed, the field operator can perform the calibration of the sensor device without the field operator moving (reciprocating) between the position where the calibration target sensor CS is installed and the position where the converting device 20 is installed. Moreover, when the sensor calibration device 10 performs the calibration of the sensor device of the calibration target, there is no need for the field operator to manually input the conversion coefficient to the converting device 20 to correct (change) it, and the conversion coefficient of the voltage-pH value conversion formula used in the conversion process by the sensor device is not corrected (changed) to an erroneous value. As described above, the sensor device of the calibration target is calibrated using the sensor calibration device 10 so that troublesome work for the field operator can be eliminated, and the sensor device can be calibrated more efficiently and accurately.

Figure 3:
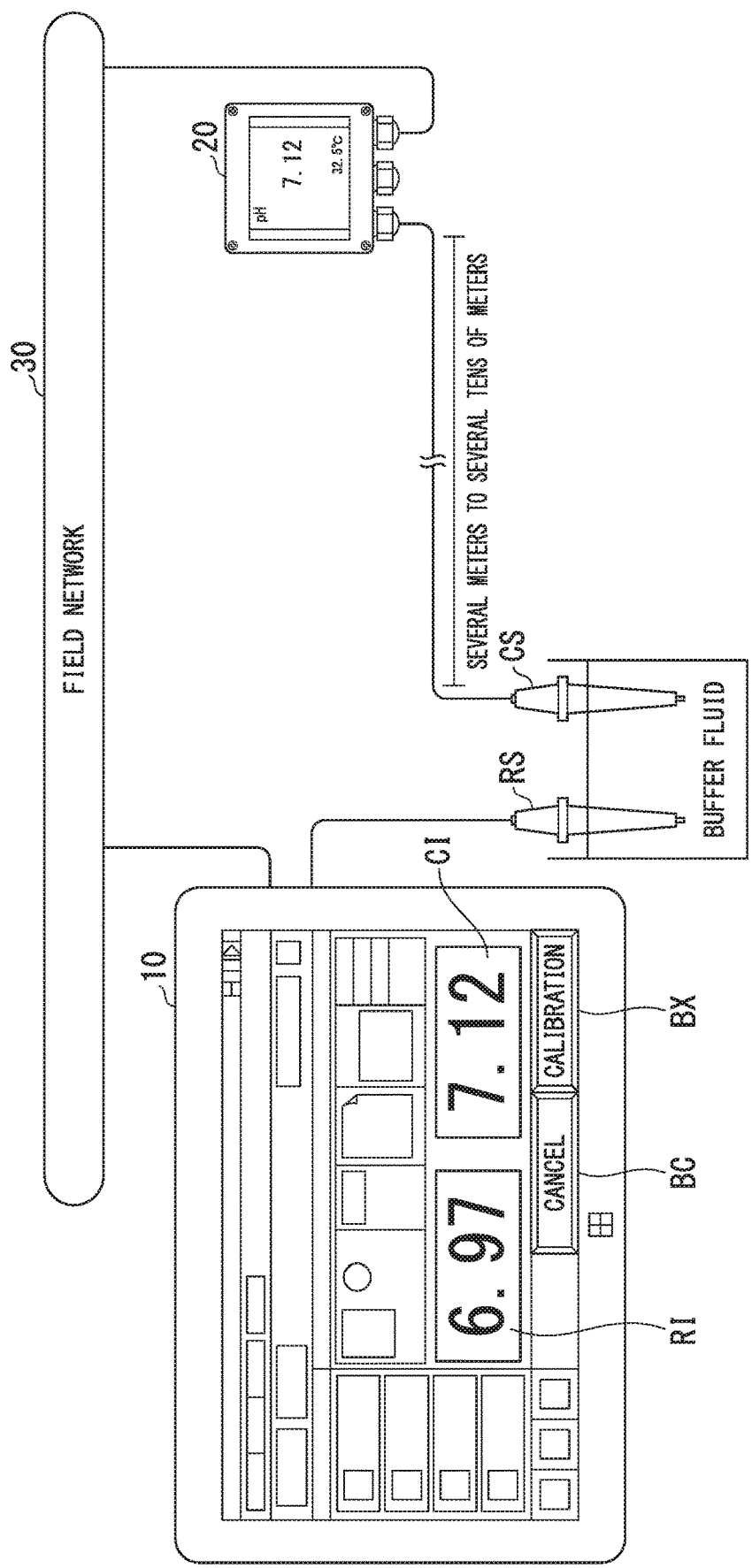
FIG. 3 is a drawing schematically showing an example of a situation in which the sensor calibration device according to the embodiment of the present invention calibrates the sensor device.
Figure 4:
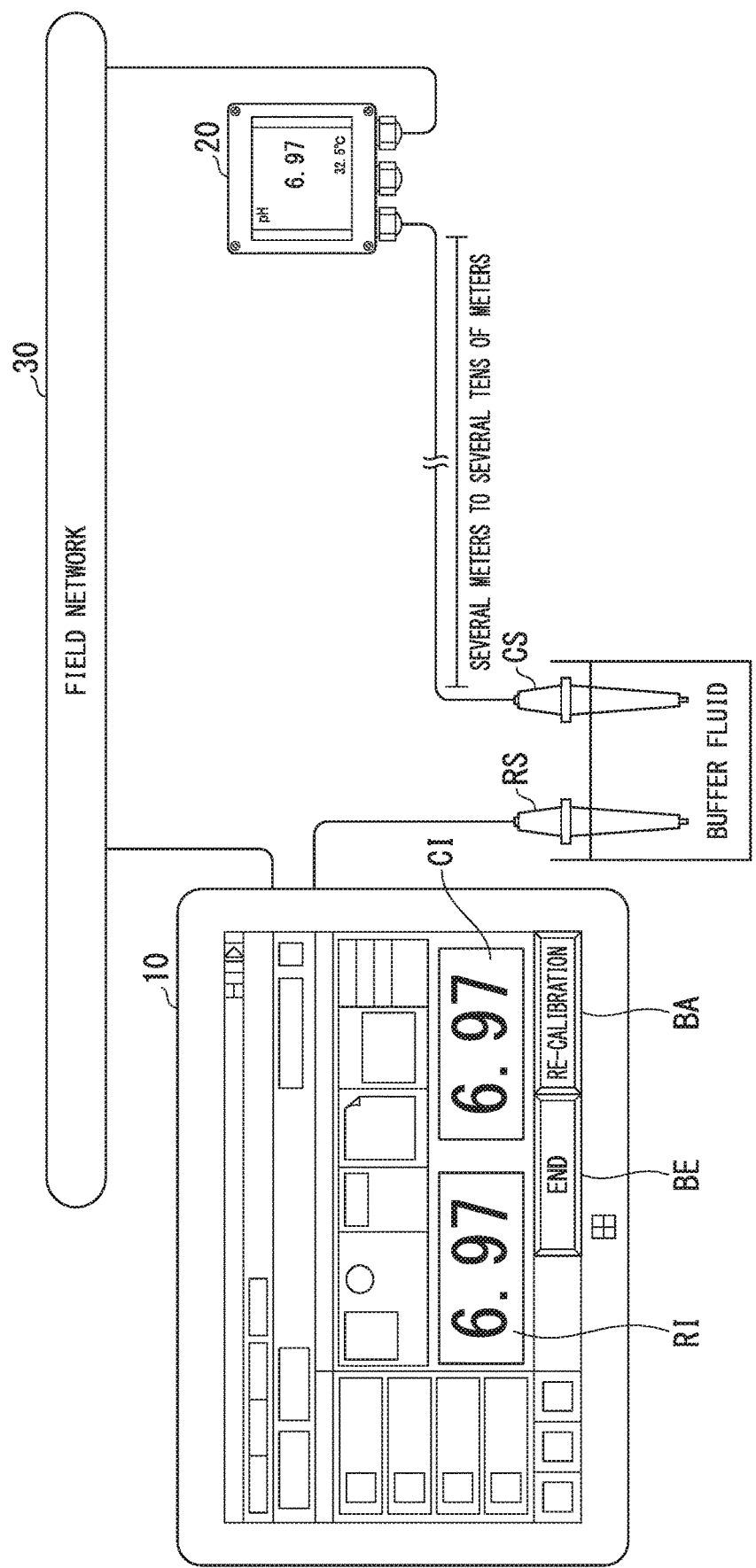
FIG. 4 is a drawing schematically showing an example of a situation in which the sensor calibration device according to the embodiment of the present invention calibrates the sensor device.

Next, an example of the calibration of the sensor device of the calibration target using the sensor calibration device 10 (in other words, the calibration process in the sensor calibration device 10) will be described. FIG. 3 and FIG. 4 are drawings showing an example of a situation in which the sensor calibration device 10 according to the embodiment of the present invention calibrates the sensor device (in other words, the sensor device including the calibration target sensor CS and the converting device 20). FIG. 3 schematically shows a situation in which both the reference sensor RS and the calibration target sensor CS are immersed in the same reference buffer fluid at the position where the calibration target sensor CS included in the sensor device of the calibration target is installed, and the sensor calibration device 10 shows the field operator the pH value measured by the sensor calibration device 10 and the pH value measured by the sensor device. In other words, FIG. 3 schematically shows a situation before the sensor calibration device 10 performs the calibration of the sensor device (before the conversion coefficient of the conversion formula (voltage-pH value conversion formula) is corrected (changed)). FIG. 4 schematically shows a situation in which the sensor calibration device 10 calibrates the sensor device of the calibration target, and the pH value measured by the sensor device becomes the same value as the pH value measured by the sensor calibration device 10. In other words, FIG. 4 schematically shows a situation after the sensor calibration device 10 has performed the calibration of the sensor device (after the conversion coefficient of the conversion formula (voltage-pH value conversion formula) is corrected (changed)).

First, a calibration process before the sensor calibration device 10 performs the calibration of the sensor device will be described with reference to FIG. 3. When the sensor calibration device 10 starts the calibration process in a state that both the reference sensor RS and the calibration target sensor CS are immersed in the reference buffer fluid, the sensor calibration device 10 displays the reference sensor information screen for showing the reference pH value (refer to step S100 and step S110). Specifically, the sensor reader 110 reads a voltage value representing the pH value of the reference buffer fluid from the reference sensor RS, the sensor manager 120 calculates the reference pH value based on the predetermined conversion formula (voltage-pH value conversion formula), and the reference information display 141 displays the reference sensor information screen for showing the reference pH value on the display device. The sensor calibration device 10 shown in FIG. 3 displays a reference sensor information screen RI indicating that the reference pH value=6.97.

Further, the sensor calibration device 10 displays a calibration target sensor information screen for showing the calibration target pH value output (transmitted) from the converting device 20 (refer to step S200 to step S220). Specifically, the sensor manager 120 outputs (transmits) a measurement value output instruction to the sensor manager 220 via the communication manager 130 and the field network 30, and the sensor manager 120 obtains the calibration target pH value output (transmitted) from the sensor manager 220. Thereafter, the calibration target information display section 142 displays the calibration target sensor information screen for showing the calibration target pH value on the display device. The converting device 20 shown in FIG. 3 displays that the calibration target pH value=7.12 which has been measured by the calibration target sensor CS. Moreover, the sensor calibration device 10 shown in FIG. 3 displays a calibration target sensor information screen CI showing that the calibration target pH value=7.12 which has been output (transmitted) from the sensor manager 220.

The field operator determines whether the calibration of the sensor device is to be executed or not based on the reference sensor information screen RI and the calibration target sensor information screen CI, and the field operator operates the sensor calibration device 10 in accordance with the result of the determination. The sensor calibration device 10 shown in FIG. 3 displays "calibration execution button BX" and "calibration cancel button BC" for receiving an operation performed by the field operator. For example, if a difference between the reference pH value displayed on the reference sensor information screen RI and the calibration target pH value displayed on the calibration target sensor information screen CI is within an allowable range, the field operator determines that the calibration of the sensor device is not to be executed. In this case, the field operator selects (for example, taps) the "calibration cancel button BC" displayed on the sensor calibration device 10, and the field operator instructs the sensor calibration device 10 not to perform the calibration of the sensor device. As a result, the sensor calibration device 10 stops the calibration of the sensor device in the calibration process in accordance with the instruction of the field operator (refer to step S300: "NO"). Moreover, for example, if the difference between the reference pH value displayed on the reference sensor information screen RI and the calibration target pH value displayed on the calibration target sensor information screen CI is out of the allowable range, the field operator determines that the calibration of the sensor device is to be executed. In this case, the field operator selects (for example, taps) the "calibration execution button BX" displayed on the sensor calibration device 10, and the field operator instructs the sensor calibration device 10 to perform calibration of the sensor device. As a result, the sensor calibration device 10 executes the calibration of the sensor device in the calibration process in accordance with the instruction of the field operator (refer to step S300: "YES").

Next, a calibration process for executing the calibration of the sensor device by the sensor calibration device 10 will be described with reference to FIG. 4. When the field operator selects the "calibration execution button BX" to instruct to execute the calibration of the sensor device, the sensor calibration device 10 executes the calibration of the sensor device, and displays the calibration target sensor information screen for displaying the calibration target pH value after calibration, which has been output (transmitted) from the calibrated converting device 20 (refer to step S310 to step S330). Specifically, the sensor manager 120 outputs (transmits) the conversion coefficient correction instruction and the conversion coefficient correction amount via the communication manager 130 and the field network 30. As a result, the sensor manager 220 provided in the converting device 20 included in the sensor device corrects (changes) the conversion coefficient of the voltage-pH value conversion formula. Thereafter, the sensor manager 220 converts, once again, the voltage value output from the calibration target sensor CS using the calibrated voltage-pH value conversion formula to calculate the calibration target pH value after calibration, and the sensor manager 220 outputs (transmits) the calculated calibration target pH value after calibration to the sensor calibration device 10 via the field network 30. The converting device 20 shown in FIG. 4 displays that the conversion coefficient of the voltage-pH value conversion formula is corrected (changed), and the voltage value representing the pH value of the reference buffer output from the calibration target sensor CS is converted into a value representing that the calibration target pH value=6.97. Thereafter, the sensor manager 120 obtains the calibration target pH value after calibration which has been output (transmitted) from the sensor manager 220, and the calibration target information display 142 displays the calibration target sensor information screen representing the calibration target pH value after calibration. The sensor calibration device 10 shown in FIG. 4 displays a calibration target sensor information screen CI for showing that the calibration target pH value (in other words, the calibration target pH value after calibration)=6.97, which has been output (transmitted) from the sensor manager 220.

The field operator determines whether or not the calibration of the sensor device has been performed correctly based on the reference sensor information screen RI and the calibration target sensor information screen CI, and the field operator operates the sensor calibration device 10 in accordance with the result of the determination. The sensor calibration device 10 shown in FIG. 4 shows "re-calibration execution button BA" and "calibration end button BE" for receiving an operation performed by the field operator. For example, if a difference between the reference pH value displayed on the reference sensor information screen RI and the calibration target pH value displayed on the calibration target sensor information screen CI is within an allowable range, the field operator determines that the calibration of the sensor device has been performed correctly. In this case, the field operator selects (for example, taps) the "calibration end button BE" displayed on the sensor calibration device 10 to instruct the sensor calibration device 10 to end the calibration of the sensor device. As a result, the sensor calibration device 10 ends the calibration of the sensor device in the calibration process in accordance with the instruction of the field operator (refer to step S400: "YES"). Moreover, for example, if the difference between the reference pH value displayed on the reference sensor information screen RI and the calibration target pH value displayed on the calibration target sensor information screen CI is within the allowable range, the field operator determines that calibration of the sensor device has been performed correctly. However, if the field operator replaces the reference buffer fluid with a reference buffer fluid of a different pH value and performs the calibration of the sensor device, the field operator selects (taps, for example) the "re-calibration execution button BA" displayed on the sensor calibration device 10 to instruct the sensor calibration device 10 to re-execute the calibration of the sensor device. As a result, the sensor calibration device 10 executes the calibration of the sensor device again in the calibration process in accordance with the instruction of the field operator (refer to step S400: "NO").

As described above, at a position where the calibration target sensor CS included in the sensor device of the calibration target is installed, the sensor calibration device 10 communicates with the converting device 20 included in the sensor device connected via the field network 30. The sensor calibration device 10 shows the field operator the reference pH value measured by the sensor calibration device 10 and the calibration target pH value measured by the sensor device of the calibration target. Then, the sensor calibration device 10 communicates with the converting device 20 connected via the field network 30 in accordance with an instruction from the field operator, and the sensor calibration device 10 corrects (changes) the conversion coefficient of the voltage-pH value conversion formula used in the conversion process by the converting device 20 so that the calibration target pH value becomes the same value as the reference pH value in order to calibrate the sensor device. Thus, in the calibration of the sensor device by the sensor calibration device 10, even if the converting device 20 included in the sensor device of the calibration target is installed away from the position where the calibration target sensor CS is installed, the calibration of the sensor device can be performed without the field operator moving (reciprocating) between the position where the target sensor CS is installed and the position where the converting device 20 is installed. In other words, by using the sensor calibration device 10, even if only one field operator performs the calibration work of the sensor device, this field operator can perform (complete) the calibration work of the sensor device of the calibration target only by operating the sensor calibration device 10 without moving (reciprocating) between the position where the target sensor CS is installed and the position where the converting device 20 is installed.

In the plant, it is also conceivable that the converting device 20 included in the sensor device of the calibration target is installed at the same position as the position where the calibration target sensor CS is installed. Even in this case, the sensor calibration device 10 corrects (changes), via the field network 30, the conversion coefficient of the voltage-pH value conversion formula used in the conversion process by the converting device 20 so that the calibration target pH value becomes the same value as the reference pH value in order to calibrate the sensor device. As a result, in the calibration of the sensor device by the sensor calibration device 10, there is no need for the field operator to manually input the conversion coefficient into the converting device 20 to perform the correction (change) work, and it can be avoided that the field operator corrects (changes) it to an erroneous conversion coefficient.

In this way, in the calibration of the sensor device of the calibration target by using the sensor calibration device 10, irrespective of the position where the converting device 20 included in the sensor device of the calibration target is installed, troublesome work for the field operator can be eliminated, and the calibration of the sensor device can be performed more efficiently and accurately.

As described above, a case where the sensor calibration device 10 calibrates the sensor device in a state of being connected to the sensor device of the calibration target via the field network 30 (in other words, a case where the sensor calibration device 10 directly performs the calibration to the sensor device connected via the field network 30) has been described. However, as described above, the field network 30 is also connected to a higher-level control system for controlling operation state of each facility in the plant. The higher-level control system may have a function of correcting (changing) the conversion coefficient of the voltage-pH value conversion formula used for the conversion process by the converting device 20. In this case, when the sensor calibration device 10 calibrates the sensor device connected via the field network 30, without directly outputting the measurement value output instruction, the conversion coefficient correction instruction, and the conversion coefficient correction amount to the sensor device, the sensor calibration device 10 may output (transmit) respective instructions to the higher-level control system, and may obtain the calibration target pH value via the higher-level control system to cause the higher-level control system to correct (change) the conversion coefficient of the voltage-pH value conversion formula. In this case, instead of the sensor manager 120 provided in the sensor calibration device 10, the higher-level control system may store information on the calibration target pH value, identification information on the calibration target sensor CS, information on date and time when the calibration of the sensor device was performed, and the conversion coefficient correction amount in association with each other, in order to manage the history of the calibration of the sensor device.

Here, in a case that the sensor manager 120 or the higher-level control system stores the calibration target pH value, the identification information on the calibration target sensor CS, the information on the date and time when the calibration of the sensor device was performed, and the conversion coefficient correction amount in association with each other, the stored information can be used as information for issuing a report of a result of the calibration of the sensor device or a calibration certificate for the sensor device, as it is (without changing and transcribing). Moreover, in a case that the sensor manager 120 or the higher-level control system manages the history of calibrating the sensor device, the managed information can be used as information for maintaining normal operation (normality) of facilities installed in the plant, such as information for diagnosing (predicting) a timing of deterioration (end of life) of the calibration target sensor CS included in the sensor device, information for diagnosing (predicting) a possibility of failure, or the like, by monitoring time-series changes in the conversion coefficient correction amount.

As described above, the sensor calibration device 10 uses the field network 30 which is a dedicated communication network constructed in the plant as a communication means, and calibrates the sensor device of the calibration target which is connected via the field network 30. However, as long as the communication means used by the sensor calibration device 10 can be connected to the sensor device of the calibration target, the form of the communication means is not limited. In other words, the sensor calibration device 10 may be directly connected to the sensor device of the calibration target by using a communication means which is in conformity with a communication standard other than the field network 30. For example, the sensor calibration device 10 may calibrate the sensor device by using the wireless communication directly connected to the sensor device of the calibration target as the communication means. An example of this case will be described below.

Figure 5:
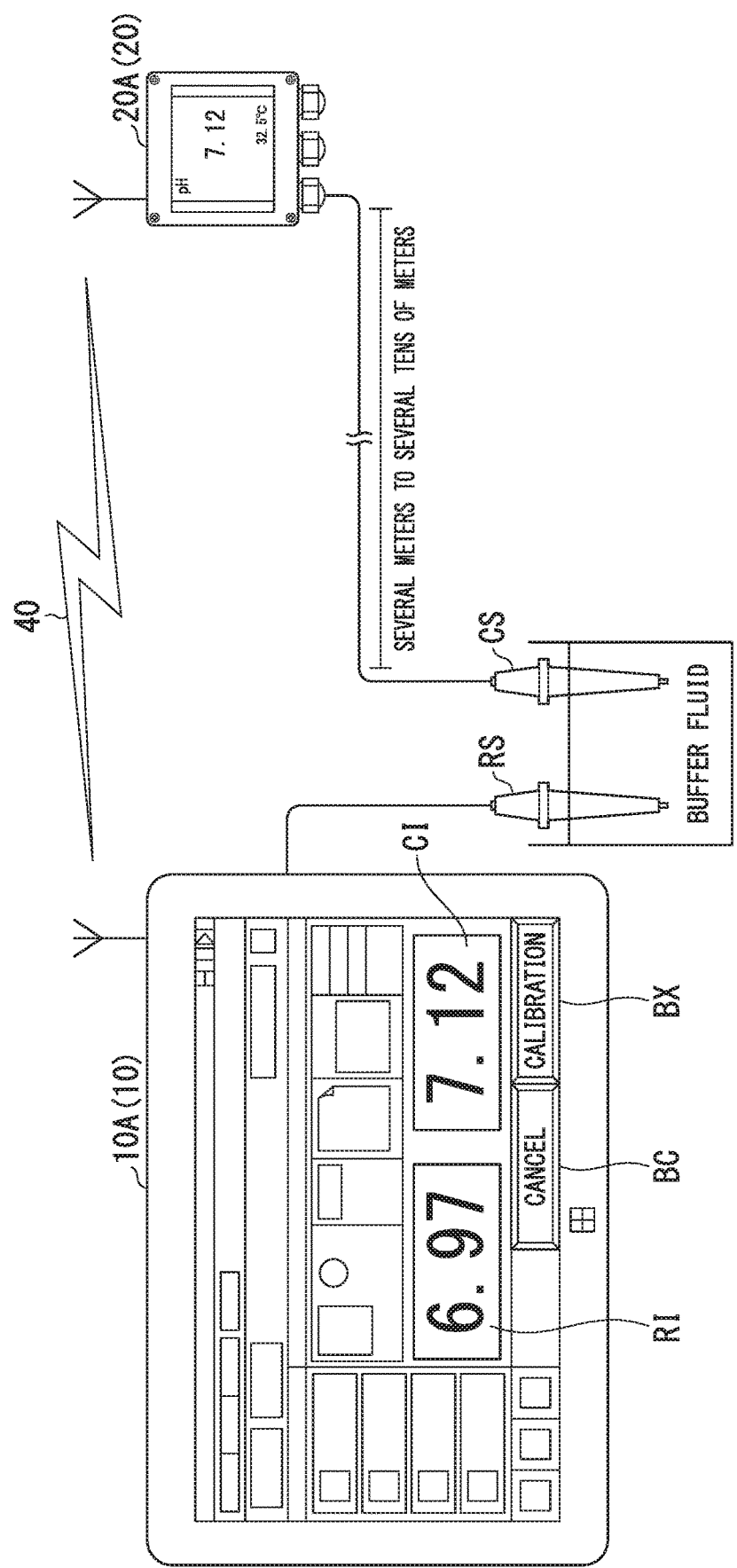
FIG. 5 is a drawing schematically showing an example of another situation in which the sensor calibration device according to the embodiment of the present invention calibrates the sensor device.
Figure 6:
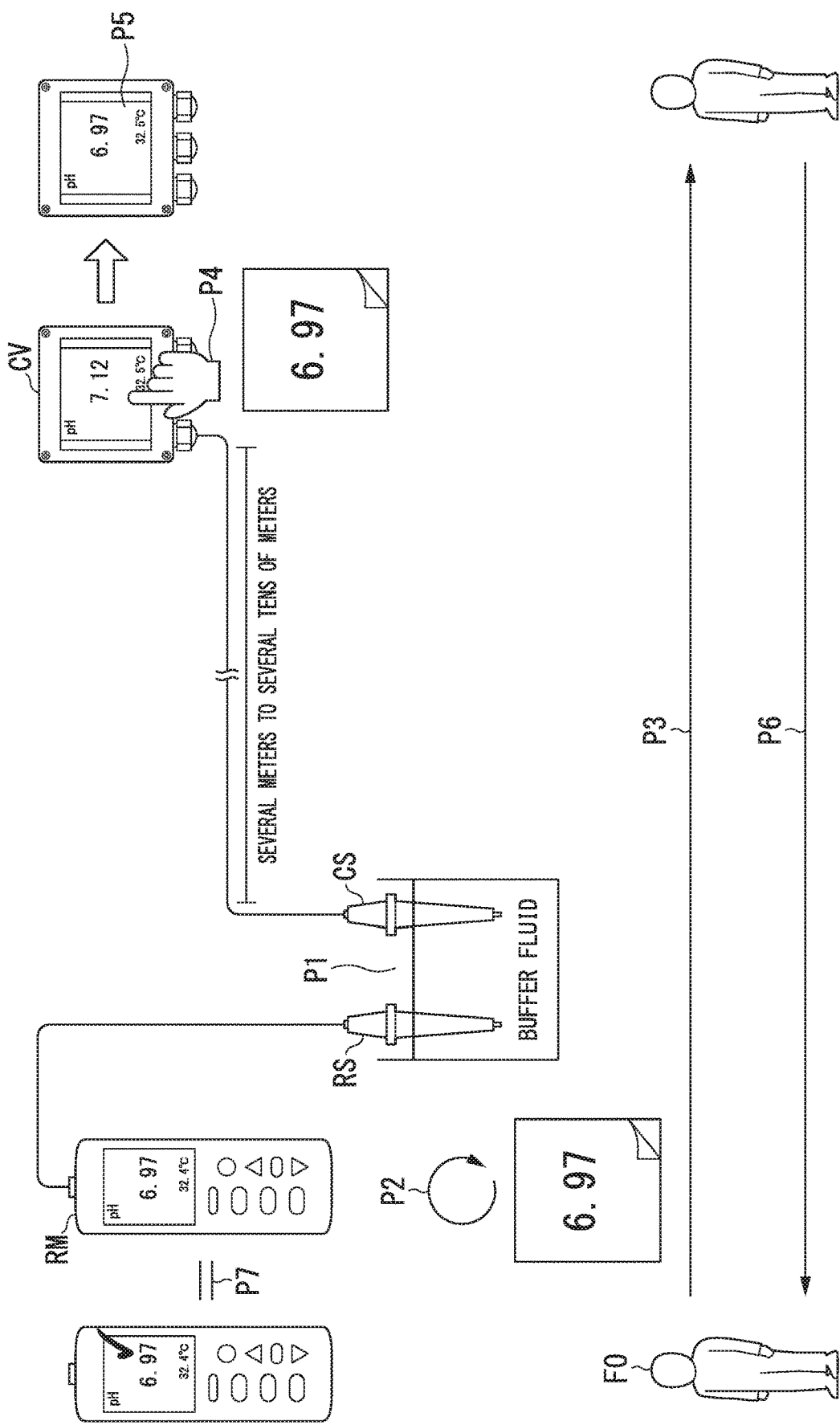
FIG. 6 is a drawing illustrating an example of a procedure of calibrating the sensor device using a conventional measuring device.

FIG. 5 schematically shows an example of another situation in which the sensor calibration device 10 according to the embodiment of the present invention calibrates the sensor device (in other words, the sensor device including the calibration target sensor CS and the converting device 20). In the example shown in FIG. 5, the sensor calibration device 10 is connected to the converting device 20 by a wireless communication 40. In other words, in the example shown in FIG. 5, the sensor calibration device 10 calibrates the sensor device of the calibration target by using the wireless communication 40 as a communication means. In the following description, in order to distinguish from the sensor calibration device 10 and the converting device 20 which are connected via the field network 30, the sensor calibration device 10 connected via the wireless communication 40 is called as "sensor calibration device 10A", and the converting device 20 connected via the wireless communication 40 is called as "converting device 20A".

Like the example shown in FIG. 3, FIG. 5 schematically shows a situation in which both the reference sensor RS and the calibration target sensor CS are immersed in the same reference buffer fluid at the position where the calibration target sensor CS included in the sensor device of the calibration target is installed, and the sensor calibration device 10A shows the field operator the pH value measured by the sensor calibration device 10A and the pH value measured by the sensor device. In other words, like the example shown in FIG. 3, FIG. 5 schematically shows a situation before the sensor calibration device 10A performs the calibration of the sensor device (before the conversion coefficient of the conversion formula (voltage-pH value conversion formula) is corrected (changed)).

The communication standards applied to the wireless communication 40 may be various types of communication standards, for example, a wireless communication standard such as a wireless LAN communication (so-called Wi-Fi (registered trademark)), a wireless communication standard of short distance such as Bluetooth (registered trademark), an infrared communication standard such as IrDA (Infrared Data Association) (registered trademark), or the like.

Like the sensor calibration device 10, the sensor calibration device 10A calibrates the sensor device connected to the sensor calibration device 10A based on a measurement value indicating a physical quantity detected and output by the reference sensor RS. However, unlike the sensor calibration device 10, the sensor calibration device 10A is connected to the sensor device of the calibration target via the wireless communication 40. The sensor calibration device 10A is different from the sensor calibration device 10 in that, among the components provided in the sensor calibration device 10 shown in FIG. 1, the communication manager 130 transmits/receives various kinds of information to/from the converting device 20A via the wireless communication 40, but its function is the same as that of the communication manager 130. The other components included in the sensor calibration device 10A are the same as the corresponding components provided in the sensor calibration device 10 shown in FIG. 1. Moreover, the converting device 20A is different from the converting device 20 in that, among the components included in the converting device 20 shown in FIG. 1, the communication manager 230 transmits/receives various kinds of information to/from the sensor calibration device 10A via the wireless communication 40, but its function is the same as that of the communication manager 230. The other components included in the converting device 20A are the same as the corresponding components provided in the converting device 20 shown in FIG. 1. Therefore, detailed descriptions of the components included in the sensor calibration device 10A and the converting device 20A and operations and functions of the components will be omitted.

Like the sensor calibration device 10, the sensor calibration device 10A also communicates with the converting device 20A included in the sensor device connected via the wireless communication 40 at a position where the calibration target sensor CS included in the sensor device of the calibration target is installed. Moreover, the sensor calibration device 10A shows the field operator the reference pH value measured by the sensor calibration device 10A and the calibration target pH value measured by the sensor device of the calibration target. Like the sensor calibration device 10, the sensor calibration device 10A also communicates with the converting device 20A connected via the wireless communication 40 in accordance with an instruction from the field operator, and the sensor calibration device 10A corrects (changes) the conversion coefficient of the voltage-pH value conversion formula used in the conversion process so that the calibration target pH value becomes the same value as the reference pH value, in order to calibrate the sensor device. As a result, like the calibration of the sensor device by the sensor calibration device 10, in the calibration of the sensor device by the sensor calibration device 10A, even if the converting device 20A included in the sensor device of the calibration target is installed away from a position where the calibration target sensor CS is installed, the field operator can perform the calibration of the sensor device without moving (reciprocating) between a position where the calibration target sensor CS is installed and a position where the converting device 20A is installed. In other words, by using the sensor calibration device 10A, even if only one field operator performs the calibration work of the sensor device, like the case using the sensor calibration device 10, this field operator can perform (complete) the calibration work of the sensor device of the calibration target only by operating the sensor calibration device 10A without moving (reciprocating) between the position where the target sensor CS is installed and the position where the converting device 20A is installed.

As described above, in the plant, it is also conceivable that the converting device 20A included in the sensor device of the calibration target is installed at the same position as the position where the calibration target sensor CS is installed. Even in this case, like the sensor calibration device 10, the sensor calibration device 10A corrects (changes), via the wireless communication 40, the conversion coefficient of the voltage-pH value conversion formula used in the conversion process by the converting device 20A in order to calibrate the sensor device. As a result, in the calibration of the sensor device by the sensor calibration device 10A, like the calibration of the sensor device by the sensor calibration device 10, there is no need for the field operator to manually input the conversion coefficient into the converting device 20A to perform the correction (change) work, and it can be avoided that the field operator corrects (changes) it to an erroneous conversion coefficient.

In this way, in the calibration of the sensor device of the calibration target by using the sensor calibration device 10A, like the calibration of the sensor device of the calibration target by using the sensor calibration device 10, irrespective of the position where the converting device 20A included in the sensor device of the calibration target is installed, troublesome work for the field operator can be eliminated, and the calibration of the sensor device can be performed more efficiently and accurately.

In the example shown in FIG. 5, the sensor calibration device 10A is connected to the converting device 20A by the wireless communication 40. In other words, in the example shown in FIG. 5, the sensor calibration device 10A uses, as a communication means, the wireless communication 40 directly connected to the sensor device of the calibration target to calibrate the sensor device of the calibration target. However, as described above, as long as the sensor calibration device 10 and the sensor device of the calibration target can be connected to each other, the form of the communication means used by the sensor calibration device 10 is not limited. Therefore, the sensor calibration device 10 may calibrate the sensor device by using, as a communication means, a wired communication directly connected to the sensor device of the calibration target. Here, a communication standard applied to the wired communication may be various types of communication standards, for example, a wired communication standard such as a wired LAN (Local Area Network), a wired interface standard such as USB (Universal Serial Bus (registered trademark)), or the like.

Configuration and operation in a case where the sensor calibration device 10 and the converting device 20 are connected to each other by a wired communication can be easily conceived from the above description. Therefore, detailed descriptions of components included in the sensor calibration device 10 and the converting device 20 connected to each other by the wired communication and operation and function of the components will be omitted.

In a case where the sensor calibration device 10 and the converting device 20 are connected by a wired communication, except for a case where the converting device 20 is installed away from a position where the calibration target sensor CS is installed, the same effect as the above description can be achieved. In other words, in a case where the sensor calibration device 10 and the converting device 20 are connected by a wire communication, it is necessary for the field operator to move (reciprocate). However, it can be avoided that the field operator corrects (changes) it to an erroneous conversion coefficient, and the calibration of the sensor device can be performed. As a method of connecting the sensor calibration device 10 and the converting device 20, in addition to the connection by a wired communication, in a case where one or both of the connection via the field network 30 and the connection via the wireless communication 40 can be performed, the same effect can be achieved. Moreover, in this case, if the converting device 20 is installed at the same position as a position where the calibration target sensor CS is installed, the field operator selects a method of connecting the sensor calibration device 10 and the converting device 20 to perform the calibration work of the sensor device.

As described above, according to the embodiment of the present invention, the sensor calibration device obtains the calibration target measurement value measured by the sensor device of the calibration target connected by the communication means, and the sensor calibration device displays the obtained calibration target measurement value together with the reference measurement value measured by the sensor calibration device. Moreover, according to the embodiment for implementing the present invention, in response to an instruction for executing the calibration of the sensor device, the sensor calibration device corrects (changes) the conversion coefficient of the conversion formula used in the conversion process in which the sensor device of the calibration target converts a physical quantity detected by the sensor into the measurement value. Thereby, it is possible to calibrate so that the calibration target measurement value output by the sensor device becomes the same value as the reference measurement value measured by the sensor calibration device. At this time, in the embodiment of the present invention, the sensor calibration device calibrates the sensor device of the calibration target connected by the communication means. Thereby, in the embodiment of the present invention, the sensor calibration device can calibrate the sensor device of the calibration target regardless of whether or not a position where the sensor is installed and a position where the converting device performing the conversion process is installed are away from each other. In other words, in the embodiment of the present invention, the sensor calibration device can calibrate the sensor device of the calibration target regardless of whether or not the sensor and the converting device are integrated with each other or separated from each other in the sensor device of the calibration target.

Specifically, in the embodiment of the present invention, the sensor calibration device 10 obtains the calibration target measurement value (in the embodiment, calibration target pH value) measured by the sensor device of the calibration target connected via the field network 30 or the wireless communication 40, which are communication means. The sensor calibration device 10 displays the obtained calibration target measurement value together with the reference measurement value (in the embodiment, reference pH value) measured by the sensor calibration device 10 in order to show it to the field operator who performs the calibration work of the sensor device in the plant. In the embodiment of the present invention, in response to the instruction of the field operator, the sensor calibration device 10 corrects (changes) the conversion coefficient of the conversion formula (in the embodiment, the voltage-pH value conversion formula) used in the conversion process in which the sensor device connected via the field network 30 or the wireless communication 40, which are communication means, converts a physical quantity (in the embodiment, pH value) detected by the sensor into the measurement value. Thereby, the sensor device can be calibrated so that the calibration target pH value output from the sensor device becomes the same value as the reference pH value measured by the sensor calibration device 10. Thereby, in the embodiment of the present invention, the sensor calibration device 10 can calibrate the sensor device regardless of whether or not a position where the sensor (in the embodiment, the calibration target sensor CS) included in the sensor device is installed and a position where the converting device (in the embodiment, the converting device 20) performing the conversion process is installed are away from each other.

Moreover, according to the embodiment of the present invention, the sensor calibration device 10 outputs (transmits), to the sensor device of the calibration target, the conversion coefficient of the conversion formula to be corrected (changed) in the calibration by using the communication means. Thereby, in the embodiment of the present invention, unlike the conventional manual calibration, the calibration of the sensor device of the calibration target can be performed without correcting (changing) it to an erroneous conversion coefficient.

As described above, according to the embodiment of the present invention, by using the sensor calibration device, it is possible to calibrate the sensor device of the calibration target installed in the facility disposed in the plant more efficiently and accurately. In the embodiment of the present invention, it is possible to eliminate troublesome work for the field operator who performs the calibration work of the sensor device in the plant. Moreover, even if only one field operator performs the calibration work of the sensor device, this field operator can perform (complete) the calibration work of the sensor device only by operating the sensor calibration device.

In the embodiment of the present invention, each of the reference sensor RS and the calibration target sensor CS is a hydrogen ion concentration (pH) sensor of glass tube type, and the measurement value (calibration target pH value), which has been measured by the calibration target sensor CS and output by the sensor device of the calibration target, is adjusted to be the same value as the measurement value (reference pH value) of the sensor calibration device 10, which has been measured by the reference sensor RS. However, if the calibration is performed using the measurement value of the sensor calibration device, which has been measured by the reference sensor of calibration standard, the sensor device of the calibration target may be a sensor device that measures any physical quantity.

For example, a program for realizing processing performed by each of the components included in the sensor calibration device 10 shown in FIG. 1 may be recorded in a computer readable storage medium, and the program recorded in the storage medium may be read and executed by a computer system, such that various steps of the processing described above according to the sensor calibration device 10 of the present embodiment may be performed. The aforementioned "computer system" may include an operating system and hardware, such as and peripheral devices. In addition, when the WWW system is utilized, the "computer system" also includes a homepage-provided environment (or a display environment). In addition, the "computer readable storage medium" denotes a writable non-volatile memory such as a flexible disk, a magneto optical disk, a ROM, and a flash memory; a portable medium such as a CD-ROM, and a storage device such as a hard disk embedded in the computer system.

Moreover, the "computer readable storage medium" includes a storage medium which retains a program for a certain time, such as a server in a case in which the program is transmitted via a network such as Internet, or a communication line such as a telephone line, and a volatile memory (for example, a dynamic random access memory (DRAM)) inside a computer system which will become a client. In addition, the program may be transmitted to a different computer system from the computer system in which the program is stored in a storage device or the like via a transmission medium or through transmission waves in the transmission medium. Here, the "transmission medium" for transmitting the program denotes a medium having a function of transmitting information, including a network (communication network) such as the internet, and a communication line such as a telephone line. In addition, the program may be provided in order to realize a part of the above-described functions. Moreover, the program may realize the above-described functions in a form of a combination with a program which has already been recorded in the computer system, that is, a so-called differential file (differential program).

As used herein, the following directional terms "front, back, above, downward, right, left, vertical, horizontal, below, transverse, row and column" as well as any other similar directional terms refer to those instructions of a device equipped with the present invention. Accordingly, these terms, as utilized to describe the present invention should be interpreted relative to a device equipped with the present invention.

The term "configured" is used to describe a component, unit or part of a device includes hardware and/or software that is constructed and/or programmed to carry out the desired function.

Moreover, terms that are expressed as "means-plus function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. A sensor calibration device for calibrating a sensor device, comprising:
   a sensor reader configured to read, from a reference sensor, a physical quantity which is a reference of a calibration and detected by the reference sensor;
   a sensor manager configured to convert the physical quantity read by the sensor reader into a reference measurement value, the sensor manager being configured to obtain a calibration target measurement value obtained by the sensor device measuring the physical quantity, and the sensor manager being configured to output, to the sensor device, a calibration instruction based on the reference measurement value and the calibration target measurement value; and
   an interface configured to show information on the reference measurement value and information on the calibration target measurement value, and the interface being configured to receive an input of a calibration execution instruction for instructing to execute the calibration of the sensor device,
   wherein the sensor manager is configured to output, to the sensor device, the calibration instruction in response to the calibration execution instruction input to the interface.

2. The sensor calibration device according to claim 1, wherein the calibration device is connected to the converting device via a dedicated communication network constructed in a plant where the sensor device is installed.

3. The sensor calibration device according to claim 1, wherein the calibration device is connected to the converting device via a wireless communication or a wired communication which is directly connected to the sensor device.

4. The sensor calibration device according to claim 1, wherein the interface is configured to generate a reference sensor information screen for showing the reference measurement value and a calibration target sensor information screen for showing the calibration target measurement value, and
   wherein the interface is configured to display the reference sensor information screen and the calibration target sensor information screen side by side.

5. A sensor calibration device for calibrating a sensor device, comprising:
   a sensor reader configured to read, from a reference sensor, a physical quantity which is a reference of a calibration and detected by the reference sensor; and
   a sensor manager configured to convert the physical quantity read by the sensor reader into a reference measurement value, the sensor manager being configured to obtain a calibration target measurement value obtained by the sensor device measuring the physical quantity, and the sensor manager being configured to output, to the sensor device, a calibration instruction based on the reference measurement value and the calibration target measurement value,
   wherein the sensor manager is configured to output, to the sensor device, the calibration instruction for instructing to correct a conversion coefficient of a conversion formula used for converting, into a measurement value, the physical quantity detected by a calibration target sensor included in the sensor device by a correction amount based on the reference measurement value and the calibration target measurement value, and the sensor manager is configured to output, to the sensor device, a conversion coefficient correction amount indicating the correction amount.

6. The sensor calibration device according to claim 5, wherein, in the sensor device, the calibration target sensor is installed away from a converting device which performs a conversion process of converting the physical quantity into the measurement value based on the conversion formula, and
   wherein the sensor manager is configured to receive the calibration target measurement value from the converting device connected to the sensor calibration device, and the sensor manager is configured to transmit the calibration instruction to the converting device.

7. The sensor calibration device according to claim 5, wherein the sensor reader is configured to read, from the reference sensor, the physical quantity in a state that both the reference sensor and the calibration target sensor are immersed in a reference buffer fluid.

8. The sensor calibration device according to claim 7, wherein the conversion formula is a voltage-pH value conversion formula for converting a voltage value output from the calibration target sensor into a pH value of the reference buffer fluid.

9. The sensor calibration device according to claim 8, wherein the sensor manager is configured to output, to the sensor device, the calibration instruction for instructing to correct an intercept and a slope of the voltage-pH value conversion formula.

10. A sensor calibration method performed by a sensor calibration device for calibrating a sensor device, comprising:
    reading from a reference sensor, by a sensor reader, a physical quantity which is a reference of a calibration and detected by the reference sensor;
    converting, by a sensor manager, the physical quantity read by the sensor reader into a reference measurement value;
    obtaining, by the sensor manager, a calibration target measurement value obtained by the sensor device measuring the physical quantity;
    outputting to the sensor device, by the sensor manager, a calibration instruction based on the reference measurement value and the calibration target measurement value;
    showing, by an interface, information on the reference measurement value and information on the calibration target measurement value;
    receiving, by the interface, an input of a calibration execution instruction for instructing to execute the calibration of the sensor device; and
    outputting to the sensor device, by the sensor manager, the calibration instruction in response to the calibration execution instruction input to the interface.

11. The sensor calibration method according to claim 10, wherein the calibration device is connected to the converting device via a dedicated communication network constructed in a plant where the sensor device is installed.

12. The sensor calibration method according to claim 10, wherein the calibration device is connected to the converting device via a wireless communication or a wired communication which is directly connected to the sensor device.

13. The sensor calibration method according to claim 10, further comprising:
    generating, by the interface, a reference sensor information screen for showing the reference measurement value and a calibration target sensor information screen for showing the calibration target measurement value; and displaying, by the interface, the reference sensor information screen and the calibration target sensor information screen side by side.

14. A sensor calibration method performed by a sensor calibration device for calibrating a sensor device, comprising:

reading from a reference sensor, by a sensor reader, a physical quantity which is a reference of a calibration and detected by the reference sensor;

converting, by a sensor manager, the physical quantity read by the sensor reader into a reference measurement value;

obtaining, by the sensor manager, a calibration target measurement value obtained by the sensor device measuring the physical quantity;

outputting to the sensor device, by the sensor manager, a calibration instruction based on the reference measurement value and the calibration target measurement value;

outputting to the sensor device, by the sensor manager, the calibration instruction for instructing to correct a conversion coefficient of a conversion formula used for converting, into a measurement value, the physical quantity detected by a calibration target sensor included in the sensor device by a correction amount based on the reference measurement value and the calibration target measurement value; and outputting to the sensor device, by the sensor manager, a conversion coefficient correction amount indicating the correction amount.

15. The sensor calibration method according to claim 14, wherein, in the sensor device, the calibration target sensor is installed away from a converting device which performs a conversion process of converting the physical quantity into the measurement value based on the conversion formula, and wherein the sensor calibration method further comprises:

receiving, by the sensor manager, the calibration target measurement value from the converting device connected to the sensor calibration device; and transmitting, by the sensor manager, the calibration instruction to the converting device.

16. The sensor calibration method according to claim 14, further comprising:

reading from the reference sensor, by the sensor reader, the physical quantity in a state that both the reference sensor and the calibration target sensor are immersed in a reference buffer fluid.

17. The sensor calibration method according to claim 16, wherein the conversion formula is a voltage-pH value conversion formula for converting a voltage value output from the calibration target sensor into a pH value of the reference buffer fluid.

18. The sensor calibration method according to claim 17, further comprising:

outputting to the sensor device, by the sensor manager, the calibration instruction for instructing to correct an intercept and a slope of the voltage-pH value conversion formula.

* * * * *